(12) United States Patent
Koob et al.

(10) Patent No.: US 10,472,409 B2
(45) Date of Patent: Nov. 12, 2019

(54) METHODS OF MAKING HIGH-STRENGTH NDGA POLYMERIZED COLLAGEN FIBERS AND RELATED COLLAGEN-PREP METHODS, MEDICAL DEVICES AND CONSTRUCTS

(71) Applicant: Shriners Hospitals for Children, Tampa, FL (US)

(72) Inventors: Thomas J. Koob, Kennesaw, GA (US); Douglas Pringle, Brandon, FL (US); Daniel Hernandez, Wesley Chapel, FL (US)

(73) Assignee: Shriners Hospitals for Children, Tampa, FL (US)

( * ) Notice: Subject to any disclaimer, the term of this patent is extended or adjusted under 35 U.S.C. 154(b) by 285 days.

(21) Appl. No.: 15/431,516

(22) Filed: Feb. 13, 2017

(65) Prior Publication Data

US 2017/0152301 A1     Jun. 1, 2017

Related U.S. Application Data

(62) Division of application No. 11/964,756, filed on Dec. 27, 2007, now Pat. No. 9,603,968.

(60) Provisional application No. 60/890,660, filed on Feb. 20, 2007, provisional application No. 60/883,408, filed on Jan. 4, 2007, provisional application No. 60/882,065, filed on Dec. 27, 2006.

(51) Int. Cl.
| | | |
|---|---|---|
| C07K 14/78 | (2006.01) | |
| A61L 27/24 | (2006.01) | |
| D06M 13/152 | (2006.01) | |
| D06M 101/14 | (2006.01) | |

(52) U.S. Cl.
CPC ............ *C07K 14/78* (2013.01); *A61L 27/24* (2013.01); *D06M 13/152* (2013.01); *D06M 2101/14* (2013.01)

(58) Field of Classification Search
None
See application file for complete search history.

(56) References Cited

U.S. PATENT DOCUMENTS

| | | | | |
|---|---|---|---|---|
| 2,747,228 A | * | 5/1956 | Braun | C09H 3/00 264/147 |
| 2,748,774 A | * | 6/1956 | Novak | A61L 17/08 28/165 |
| 3,316,699 A | | 5/1967 | Mattingly | |

(Continued)

FOREIGN PATENT DOCUMENTS

| | | |
|---|---|---|
| CA | 2285161 | 5/1996 |
| EP | 1493404 | 1/2005 |

(Continued)

OTHER PUBLICATIONS

Becker et al. "Early active motion following a beveled technique of flexor tendon repair: Report on fifty cases" *Journal of Hand Surgery*, 1979, vol. 4 No. 5, pp. 454-460.

(Continued)

*Primary Examiner* — Cachet I Proctor
(74) *Attorney, Agent, or Firm* — Myers Bigel, P.A.

(57) ABSTRACT

The disclosure describes methods of making high-strength NDGA collagen and associated methods of preparing collagen preparatory material and medical bioprostheses.

15 Claims, 7 Drawing Sheets

(56) References Cited

U.S. PATENT DOCUMENTS

| | | | |
|---|---|---|---|
| 4,581,030 A * | 4/1986 | Bruns | A61F 2/14 |
| | | | 128/DIG. 8 |
| 4,590,928 A | 5/1986 | Hunt et al. | |
| 4,792,336 A | 12/1988 | Hlavacek et al. | |
| 4,841,962 A | 6/1989 | Berg et al. | |
| 4,883,486 A | 11/1989 | Kapadia et al. | |
| 4,979,956 A | 12/1990 | Silvestrini | |
| 5,078,744 A | 1/1992 | Chvapil | |
| 5,106,949 A | 4/1992 | Kemp et al. | |
| 5,171,273 A | 12/1992 | Silver et al. | |
| 5,256,418 A | 10/1993 | Kemp et al. | |
| 5,263,984 A | 11/1993 | Li et al. | |
| 5,378,469 A | 1/1995 | Kemp et al. | |
| 5,656,605 A | 8/1997 | Hansson et al. | |
| 5,713,374 A | 2/1998 | Pachence et al. | |
| 5,718,012 A | 2/1998 | Cavallaro | |
| 5,718,717 A | 2/1998 | Bonutti | |
| 6,090,117 A | 7/2000 | Shimizu | |
| 6,090,910 A | 7/2000 | Shinoda et al. | |
| 6,224,630 B1 | 5/2001 | Bao et al. | |
| 6,277,397 B1 | 8/2001 | Shimizu | |
| 6,280,474 B1 | 8/2001 | Cassidy et al. | |
| 6,292,697 B1 | 9/2001 | Roberts | |
| 6,335,007 B1 | 1/2002 | Shimizu et al. | |
| 6,531,147 B2 | 3/2003 | Sawhney et al. | |
| 6,565,960 B2 | 5/2003 | Koob et al. | |
| 6,589,257 B1 | 7/2003 | Shimizu | |
| 6,592,623 B1 | 7/2003 | Bowlin et al. | |
| 6,645,247 B2 | 11/2003 | Ferree | |
| 6,692,528 B2 | 2/2004 | Ward et al. | |
| 6,713,537 B1 | 3/2004 | Ueda et al. | |
| 6,730,124 B2 | 5/2004 | Steiner | |
| 6,752,831 B2 | 6/2004 | Sybert et al. | |
| 6,821,530 B2 | 11/2004 | Koob et al. | |
| 6,936,072 B2 | 8/2005 | Lambrecht et al. | |
| 6,955,683 B2 | 10/2005 | Bonutti | |
| 7,084,082 B1 | 8/2006 | Shimizu | |
| 7,090,690 B2 | 8/2006 | Foerster et al. | |
| 7,115,146 B2 | 10/2006 | Boyer, II et al. | |
| 7,135,040 B2 | 11/2006 | Wang et al. | |
| 7,309,359 B2 | 12/2007 | Trieu et al. | |
| 7,354,627 B2 | 4/2008 | Pedrozo et al. | |
| 2001/0018619 A1 | 8/2001 | Enzerink et al. | |
| 2002/0037940 A1* | 3/2002 | Koob | C08H 1/06 |
| | | | 521/55 |
| 2002/0123805 A1 | 9/2002 | Murray et al. | |
| 2003/0100108 A1 | 5/2003 | Altman et al. | |
| 2003/0230316 A1 | 12/2003 | Glucksman et al. | |
| 2004/0110439 A1 | 6/2004 | Chaikof et al. | |
| 2004/0131562 A1 | 7/2004 | Gower et al. | |
| 2004/0193241 A1 | 9/2004 | Stinson | |
| 2004/0224406 A1 | 11/2004 | Altman et al. | |
| 2004/0267362 A1 | 12/2004 | Hwang et al. | |
| 2006/0095134 A1 | 5/2006 | Trieu et al. | |
| 2006/0257377 A1 | 11/2006 | Atala et al. | |
| 2006/0263417 A1 | 11/2006 | Lelkes et al. | |
| 2007/0118217 A1 | 5/2007 | Brulez et al. | |
| 2007/0134305 A1 | 6/2007 | Zilberman | |
| 2007/0248643 A1 | 10/2007 | Devore et al. | |
| 2008/0020012 A1 | 1/2008 | Ju et al. | |
| 2008/0038352 A1 | 2/2008 | Simpson et al. | |
| 2008/0124371 A1 | 5/2008 | Turos et al. | |
| 2008/0188933 A1 | 8/2008 | Koob et al. | |
| 2008/0200992 A1 | 8/2008 | Koob et al. | |
| 2008/0215150 A1 | 9/2008 | Koob et al. | |
| 2009/0216233 A1 | 8/2009 | Wiedrich et al. | |
| 2009/0287308 A1 | 11/2009 | Davis et al. | |

FOREIGN PATENT DOCUMENTS

| | | |
|---|---|---|
| WO | WO 96/14095 | 5/1996 |
| WO | WO 2001/007241 | 10/2001 |
| WO | WO 2008/041183 | 4/2008 |

OTHER PUBLICATIONS

Brunelli et al. "Slip-knot flexor tendon suture in zone II allowing immediate mobilisation" *The Hand* 1983, vol. 15, pp. 352-358.

Conair QB3ECS Quick Braid Styling Kit, *Product advertisement* © 2007 (1 page).

Greis et al. "The influence of tendon length and fit on the strength of the tendon-bone tunnel complex" *Am. J. Sports Med.*, 2001, 29:493-497.

Grog, The Reef (Square) Knot, Animated Knots by Grog, downloaded at http://www.animatedknots.com/reef/index.php, on May 28, 2009 using WayBack Machine on www.archive.org for publication date of Dec. 26, 2005.

Integra™ NeuraGen™ Nerve Guide, Product Broacher, 4 pages (2005).

Integra™ NeuraGen™ Nerve Guide, Product Webpage, http://www.integra-ls.com/products/?product=88, Date unknown but believed to be prior to the filing date of the present application, 2 pages.

Integra™ NeuraWrap™ Nerve Protector, Product Webpage, http://www.integra-ls.com/products/?product=198, Date unknown but believed to be prior to the filing date of the present application, 2 pages.

International Search Report and the Written Opinion of the International Searching Authority corresponding to International Patent Application No. PCT/US2007/026361 (dated Apr. 8, 2009).

Invitation to Pay Additional Fees corresponding to International Patent Application No. PCT/US2007/026361 (dated Apr. 24, 2009).

Koob et al. "Biocompatibility of NDGA-polymerized collagen fibers. I. Evaluation of cytotoxicity with tendon fibroblasts in vitro" © 2001John Wiley & Sons, Inc.

Koob et al. "Biocompatibility of NDGA-polymerized collagen fibers. II. Attachment, proliferation, and migration of tendon fibroblasts in vitro" © 2001John Wiley & Sons, Inc.

Koob et al. "Biomimetic approaches to tendon repair" *Comp. Biochem. Physiol. A Mol. Integr. Phys.*, 2002, 133: 1171-1192.

Koob et al. "Material properties of NDGA-collagen composite fibers: development of biologically based tendon constructs" *Biomaterials*, 2002, 23:202-212.

Koob et al. "Mechanical and thermal properties of novel polymerized NDGA-gelatin hydrogels" *Biomaterials*, 2002, 24:1285-1292.

Martin et al. "Anterior Cruciate Ligament Graft Preparation: A New and Quick Alternative to the Whipstitch" *Arthroscopy: The Journal of Arthroscopic & Related Surgery*, Online Publication Date of Nov. 29, 2006.

Messina "The double armed suture: Tendon repair with immediate mobilization of the fingers" *Journal of Hand Surgery*, 1992, 17A:137-142.

Nottage et al. "Arthoscopic Knot Tying Techniques" *Arthroscopy: The Journal of Arthroscopic & Related Surgery* 15(1999): 515-521.

Powell et al. "Forces transmitted along human flexor tendons during passive and active movements of the fingers" *J. Hand Surg.*, 2004, 29:4:386-389.

Rodeo et al. "Tendon healing in a bone tunnel. A biomechanical and histological study in a dog" *J. Bone Joint Surg.*, 1993, 75:1795-1803.

Savage et al. "Flexor tendon repair using a "six strand" method of repair and early active mobilisation" *Journal of Hand Surgery*, (British vol., 1989), 14B:396-399.

Silva et al. "The insertion site of the canine flexor digitorum profundus tendon heals slowly following injury and suture repair" *J. Orthop. Res.*, 2002, 20:447-453.

Trotter et al. "Molecular structure and functional morphology of echinoderm collagen fibrils" *Cell Tiss. Res.*, 1994, 275: 451-458.

* cited by examiner

METHODS OF MAKING HIGH-STRENGTH NDGA POLYMERIZED COLLAGEN FIBERS AND RELATED COLLAGEN-PREP METHODS, MEDICAL DEVICES AND CONSTRUCTS

RELATED APPLICATIONS

This application is a divisional of U.S. application Ser. No. 14/964,756, filed Dec. 27, 2007, which claims the benefit of priority to U.S. Provisional Application Ser. No. 60/882,065, filed Dec. 27, 2006, U.S. Provisional Application Ser. No. 60/883,408, Filed Jan. 4, 2007, and U.S. Provisional Application No. 60/890,660, filed Feb. 20, 2007, the contents of which are hereby incorporated by reference as if recited in full herein.

FIELD OF THE INVENTION

The invention relates to biomedical materials.

BACKGROUND OF THE INVENTION

Koob et al. have described methods of producing nordihydroguaiaretic acid (NDGA) polymerized collagen fibers of tensile strengths similar to that of natural tendon (e.g., about 91 MPa) to make medical constructs and implants. See, Koob and Hernandez, *Material properties of polymerized NDGA-collagen composite fibers: development of biologically based tendon constructs*, Biomaterials 2002 January; 23 (1): 203-12, and U.S. Pat. No. 6,565,960, the contents of which are hereby incorporated by reference as if recited in full herein.

SUMMARY OF EMBODIMENTS OF THE INVENTION

Embodiments of the present invention are directed to improved methods of producing biocompatible NDGA polymerized fibers. Some embodiments are directed at producing high-strength NDGA polymerized fibers used to make implantable biocompatible constructs, implants and/or other prostheses.

Some embodiments are directed to methods of manufacturing nordihydroguaiaretic acid (NDGA) polymerized collagen fibers. The methods include: (a) treating collagen with a solution comprising NDGA; (b) drying the NDGA treated collagen while holding the collagen in tension for a period of time; (c) washing the dried NDGA treated collagen in a solution to remove unreacted soluble NDGA cross-linking intermediates; (d) drying the NDGA treated collagen while holding the collagen in tension for a period of time; and (e) repeating steps (a)-(d) at least once to produce high-strength NDGA polymerized collagen fibers.

In some embodiments, the methods can also include, after steps (a)-(d) are repeated at least once, forming a bioprosthesis using the high strength NDGA polymerized fibers. In some embodiments, the bioprosthesis can be a ligament bioprosthesis that has a tensile strength of between about 180-280 MPa, and a stiffness and dynamic flexibility that meets or exceeds that of a natural ligament. In other embodiments, the bioprosthesis can be a tensile strength between about 180-280 MPa, and a stiffness and dynamic flexibility that meets or exceeds that of a natural tendon.

Still other embodiments are directed to biomedical implants. The implants include at least one high-strength synthetic NDGA polymerized collagen fiber.

In some embodiments, the at least one fiber is a plurality of fibers, and the bioprosthesis is a ligament bioprosthesis that has a tensile strength of between about 180-300 MPa, and a stiffness and dynamic flexibility that meets or exceeds that of a natural ligament. In other embodiments, the at least one fiber is a plurality of fibers, and the bioprosthesis has a tensile strength between about 180-300 MPa, and a stiffness and dynamic flexibility that meets or exceeds that of a natural tendon.

Yet other embodiments are directed to medical kits for a tendon or ligament repair, augmentation or replacement. The kits include a high-strength NDGA collagen fiber construct and a sterile package sealably enclosing the NDGA collagen fiber construct therein.

Among other things, the NDGA collagen fiber construct can be a ligament bioprosthesis that has a tensile strength of between about 180-300 MPa a tendon bioprosthesis that has a tensile strength of between about 180-300 MPa.

Still other embodiments are directed to medical kits that include an implantable medical device comprising NDGA collagen fiber derived from echinoderm collagen; and a sterile package sealably enclosing the device therein. The NDGA collagen fibers may have an average tensile strength of about 100 MPa.

Additional embodiments are directed to medical kits that include a device comprising NDGA collagen fiber derived from porcine collagen and a sterile package sealably enclosing the device therein. The NDGA collagen fibers may be high-strength fibers.

Other embodiments are directed to medical kits that include a device comprising NDGA collagen fiber derived from caprine collagen and a sterile package sealably enclosing the device therein. The NDGA collagen fibers may be high-strength fibers.

Other embodiments are directed to methods of organizing collagen before cross-linking. The methods include: (a) purifying donor collagen preparatory material; (b) dialyzing the purified collagen preparatory material a plurality of times; and (c) forming a substantially clear gel using the dialyzed collagen material thereby indicating improved organization of collagen fibrils.

The dialyzing can be carried out three times against dionized water (DI) in a volume ration of between about 30:1 to about 100:1, for between about 30-90 minutes. Typically, each dialyzing is carried out against dionized water (DI) in a volume ration of about 60 to 1 for about 40 minutes.

Further features, advantages and details of the present invention will be appreciated by those of ordinary skill in the art from a reading of the figures and the detailed description of the embodiments that follow, such description being merely illustrative of the present invention.

DETAILED DESCRIPTION

Figure 1:
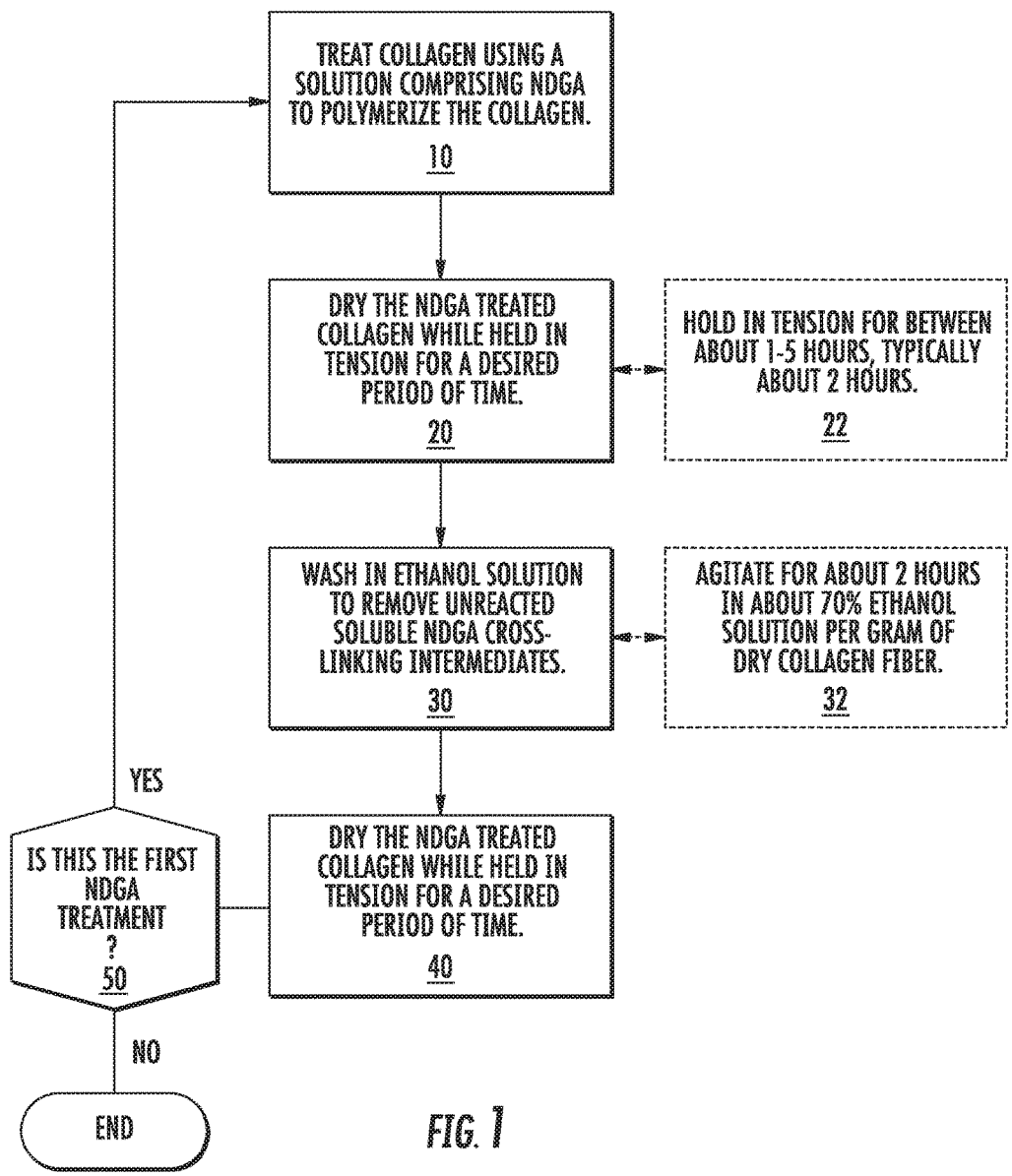
FIG. 1 is a flow chart of operations that can be used to carry out embodiments of the invention.

The present invention now is described more fully hereinafter with reference to the accompanying drawings, in which embodiments of the invention are shown. This invention may, however, be embodied in many different forms and should not be construed as limited to the embodiments set forth herein; rather, these embodiments are provided so that this disclosure will be thorough and complete, and will fully convey the scope of the invention to those skilled in the art.

Like numbers refer to like elements throughout. In the figures, the thickness of certain lines, layers, components, elements or features may be exaggerated for clarity. Broken lines illustrate optional features or operations unless specified otherwise.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. As used herein, phrases such as "between X and Y" and "between about X and Y" should be interpreted to include X and Y. As used herein, phrases such as "between about X and Y" mean "between about X and about Y." As used herein, phrases such as "from about X to Y" mean "from about X to about Y."

Unless otherwise defined, all terms (including technical and scientific terms) used herein have the same meaning as commonly understood by one of ordinary skill in the art to which this invention belongs. It will be further understood that terms, such as those defined in commonly used dictionaries, should be interpreted as having a meaning that is consistent with their meaning in the context of the specification and relevant art and should not be interpreted in an idealized or overly formal sense unless expressly so defined herein. Well-known functions or constructions may not be described in detail for brevity and/or clarity.

It will be understood that when an element is referred to as being "on", "attached" to, "connected" to, "coupled" with, "contacting", etc., another element, it can be directly on, attached to, connected to, coupled with or contacting the other element or intervening elements may also be present. In contrast, when an element is referred to as being, for example, "directly on", "directly attached" to, "directly connected" to, "directly coupled" with or "directly contacting" another element, there are no intervening elements present. It will also be appreciated by those of skill in the art that references to a structure or feature that is disposed "adjacent" another feature may have portions that overlap or underlie the adjacent feature.

It will be understood that, although the terms first, second, etc. may be used herein to describe various elements, components, regions, layers and/or sections, these elements, components, regions, layers and/or sections should not be limited by these terms. These terms are only used to distinguish one element, component, region, layer or section from another region, layer or section. Thus, a first element, component, region, layer or section discussed below could be termed a second element, component, region, layer or section without departing from the teachings of the present invention. The sequence of operations (or steps) is not limited to the order presented in the claims or figures unless specifically indicated otherwise.

The terms "implant" and "prosthesis" are used interchangeably herein to designate a product configured to repair or replace (at least a portion of) a natural tendon, ligament or other tissue of a mammalian subject (for veterinary or medical (human) applications). The term "implantable" means the device can be inserted, embedded, grafted or otherwise chronically attached or placed on or in a patient. The term "agitate" and derivatives thereof refer to mixing the components in a vessel by moving, shaking, vibrating, oscillating, rotating, centrifuging or other movement types, including combinations of the movement types.

The term "dynamic flexibility" means that the bioprosthesis is able to perform at least as well as the target tissue undergoing repair, such as a natural ligament or tendon, so as to be able to dynamically stretch and compress, and typically allow some torsion, to behave at least as well as the repaired or replaced target tissue.

The collagen can be of any form and from any origin. The collagen can be any of the identified collagen genotypes, for example, the interstitial fiber forming collagen types I, II and III, as well as any other substantially fiber forming types of collagen, for example collagen VI. The collagen can be acid soluble collagen or pepsin solubilized collagen. The collagen can be from mammalian cells synthesized in vitro. The collagen can be from molecularly engineered constructs and synthesized by bacterial, yeast or any other molecularly manipulated cell type. For example, the collagen can be sea cucumber dermis collagen, bovine, caprine, porcine, ovine or other suitable donor mammal, marine animal collagen such as chinoderms, molecularly engineered collagen, or gelatin (e.g., in any suitable form including solid, gel, hydrogels, liquids, or foams). In addition, the collagen can be digested with a protease before the oxidizing and polymerizing steps. The collagen can be in the form of microfibrils, fibrils, natural fibers, or synthetic fibers. The polymeric material, e.g., collagen, can be solubilized, dissolved or otherwise transferred into an acid solution, for example, acetic acid (e.g., about 0.01M to about 1.0M, typically about 0.5M), hydrochloric acid (between about pH 1 to about pH 3, typically about pH 2.0), or any other suitable acid at appropriate concentration (e.g., about pH 1.0 to about pH 3.0, typically about pH 2.0). The collagen can also be dissolved in a neutral buffered solution either with or without salts, e.g., phosphate buffer at about pH 7.0, phosphate buffered saline at about pH 7.0. The phosphate buffer can be at any concentration of sodium phosphate between about 0.01 and 0.5, but more typically between about 0.02 and about 0.1M. The buffer can also be any buffer, including, but not limited to, sodium acetate, HEPES, or MOPS. The collagen can be present in a quantity that is at least about 0.1% to about 10%, typically between 0.1% to about 5%

(e.g, about 0.1, 0.2, 0.3, 0.4, 1.0, 2.0, 4.0%) by weight per volume before dialyzing, or by weight per volume in the neutral buffer solution before fibrillogenesis and fiber formation. In the dried fiber, collagen can be between about 50-100% (e.g., at least about 75%, 90%, 95% or 100%) before crosslinking.

Collagen "microfibrils," "fibrils," "fibers," and "natural fibers" refer to naturally-occurring structures found in a tendon. Microfibrils are about 3.5 to 50 nm in diameter. Fibrils are about 50 nm to 50 μm in diameter. Natural fibers are above 50 μm in diameter. A "synthetic fiber" refers to any fiber-like material that has been formed and/or chemically or physically created or altered from its naturally-occurring state. For example, an extruded fiber of fibrils formed from a digested tendon is a synthetic fiber but a tendon fiber newly harvested from a mammal is a natural fiber. Of course, synthetic collagen fibers can include non-collagenous components, such as particulates, hydroxyapatite and other mineral phases, or drugs that facilitate tissue growth or other desired effects. See, U.S. Pat. No. 6,821,530, incorporated herein by reference above. For example, the fibers and/or constructs formed from same, can include compositions that can contain carbon nano-tubes, zinc nano-wires, nano-crystalline diamond, or other nano-scale particulates; and larger crystalline and non-crystalline particulates such as calcium phosphate, calcium sulfate, apatite minerals. For example, the compositions can contain therapeutic agents such as bisphosphonates, anti-inflammatory steroids, growth factors such as basic fibroblast growth factor, tumor growth factor beta, bone morphogenic proteins, platelet-derived growth factor, and insulin-like growth factors; chemotactic factors such fibronectin and hyaluronan; and extracellular matrix molecules such as aggrecan, biglycan, decorin, fibromodulin, COMP, elastin, and fibrillin. In some embodiments, the fibers and/or fiber-derived constructs can contain cells, engineered cells, stem cells, and the like. Combinations of the above or other materials can be embedded, coated and/or otherwise attached to the fibers and/or construct formed from same.

Properly processed NDGA polymerized fibers are biocompatible as discussed in U.S. Pat. No. 6,565,960, incorporated by reference hereinabove. FIG. 1 illustrates operations that can be used to form high-strength collagen fibers. The term "high-strength" refers to fibers having an average tensile strength of at least about 150 MPa, such as between about 180 MPa and 350 MPa, and typically, for bovine, porcine or caprine based "donor" collagen, between about 180 MPa and 280 MPa, such as about 279 MPa (measured on average). The fibers may also have suitable stiffness and strain yield. In general, the fibers formed from the compositions and processes of the invention can have a stiffness of at least about 200 MPa (e.g., at least about 300, 400, 500, or 600 MPa), and a strain at failure of less than about 20% (e.g., less than about 15 or 10%). The fibers may be formed with a relatively thin diameter, such as, for example about a 0.08 mm dry diameter (on average) and about a 0.13 mm wet diameter (on average).

To measure these physical properties, any suitable apparatus having (1) two clamps for attaching to the fiber(s), (2) a force transducer attached to one of the clamps for measuring the force applied to the fiber, (3) a means for applying the force, and (4) a means for measuring the distance between the clamps, is suitable. For example, tensiometers can be purchased from manufacturers MTS, Instron, and Cole Farmer. To calculate the tensile strength, the force at failure is divided by the cross-sectional area of the fiber through which the force is applied, resulting in a value that can be expressed in force (e.g., Newtons) per area. The stiffness is the slope of the linear portion of the stress/strain curve. Strain is the real-time change in length during the test divided by the initial length of the specimen before the test begins. The strain at failure is the final length of the specimen when it fails minus the initial specimen length, divided by the initial length.

An additional physical property that is associated with the extent of cross-linking in a composition is the shrinkage temperature. In general, the higher the temperature at which a collagenous composition begins to shrink, the higher the level of cross-linking. The shrinkage temperature of a fiber can be determined by immersing the fiber in a water or buffer bath, raising the temperature of the water or buffer bath, and observing the temperature of the water or buffer bath at which the fiber shrinks. Tension on the fiber may be required for observing the shrinkage. The shrinking temperature for the compositions of the invention can be at least about 60 degrees C. (e.g., at least 65 or 70 degrees C.).

For compositions that are not elongated in shape, such as in a disk, the fracture pressure in compression loading can be an indication of physical strength. The fracture pressure is the minimum force per area at which a material cracks.

It is believed that high-strength fibers allow for improved or alternative bioprosthesis constructs and/or medical devices. For example, high-strength fibers may be particularly suitable for bioprostheses suitable for tendon and/or ligament repair, augmentation, and/or replacement. A biomaterial with increased strength over that of natural tissue (muscle and the like) can allow for a bioprosthesis that has a smaller cross-sectional area than that of the natural tissue being replaced or repaired. The smaller area can improve the function of the bioprosthesis as a scaffold for neo-tendon or ligament in-growth, which may augment strength and/or long term survival rate of the repair. The use of high-strength fibers on medical devices and constructs may also offset or reduce the effects of stress concentration factors that reside at regions of integration in adjacent tissue such as bone.

Referring to FIG. 1, some methods include obtaining or harvesting pepsin-solubilized collagen from a donor source. The harvested collagen can be treated using a solution comprising NDGA to polymerize the collagen (block 10). The NDGA treated collagen can then be dried while the collagen is held in tension for a desired period of time (block 20). The typical tension force during at least part of the drying operation is between about 2-4 grams weight per fiber. The "dried" collagen can then be placed in a liquid bath or solution (typically an ethanol solution) and washed to remove any unreacted soluble NDGA cross-linking intermediates (block 30). That is, after the NDGA polymerization process, the NDGA treated collagen fibers can be washed in an ethanol solution (typically including phosphate buffered saline) to remove potential cytotoxins due to leachable reaction products. After washing, the collagen can then be dried again while held in tension (block 40). This sequence can be repeated at least once (block 50); typically only two repetitions are needed to achieve the desired tensile strength.

The drying may be at room temperature, typically at between about 50° F. (10° C.) to about 80° F. (27° C.) or may be carried out at suitable, low heating temperatures, below about 105° F. (40.6° C.), with or with out the aid of forced gas flow (e.g., fans to blow air). Different drying times and temperatures may be used during a single drying event or between drying events. The drying can be carried out in a sterile and/or suitable clean-room environment and/or sterilized after the process is completed before or after packaging. The collagen may be partially or substantially totally dried. In some embodiments, the collagen is not required to be completely dry before the next step. The desired period of drying time can be between about 1-5 hours, typically about 2 hours for a typical amount of collagen (block 22). The washing can include agitating the NDGA-treated collagen in a solution of between about 50-95% ethanol, typically about 70% ethanol, in an amount of at least about 50 ml of 70% ethanol per gram of dry fiber.

Figure 4:
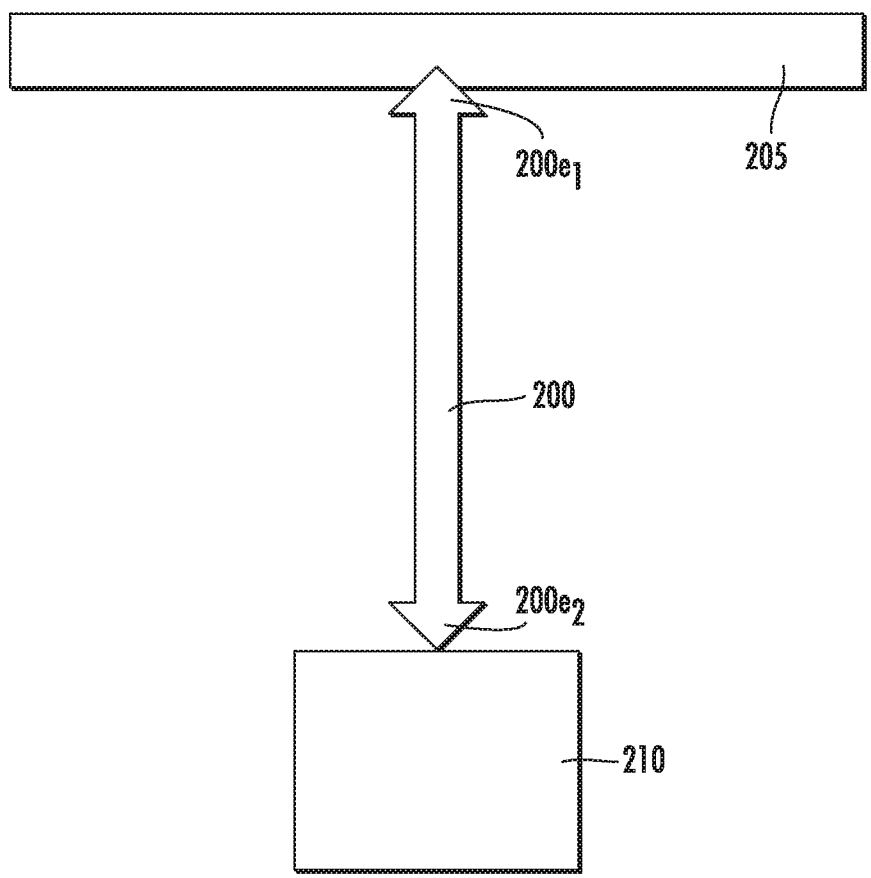
FIG. 4 is a schematic illustration of an NDGA-treated fiber held in tension during a drying operation according to embodiments of the present invention.

The tensile force can be provided as shown in FIG. 4, by clamping, pinching, rolling or otherwise attaching one end portion $200e_1$ of a fiber 200 to a rod or other holding member 205 and attaching at least one weight 210 to an opposing end portion $200e_2$. A single weight may be used for more than one fiber or each fiber may use more than one weight. Other tensioning mechanisms or configurations may also be used. Substantially horizontal, angled or other non-vertically oriented tensioning systems may be used. In some embodiments, weights can be applied to both opposing end portions of the fiber(s) to generate the desired tension. A typical weight of about 2-10 grams per fiber, depending on the extruded fiber size, can be appropriate.

Figure 2:
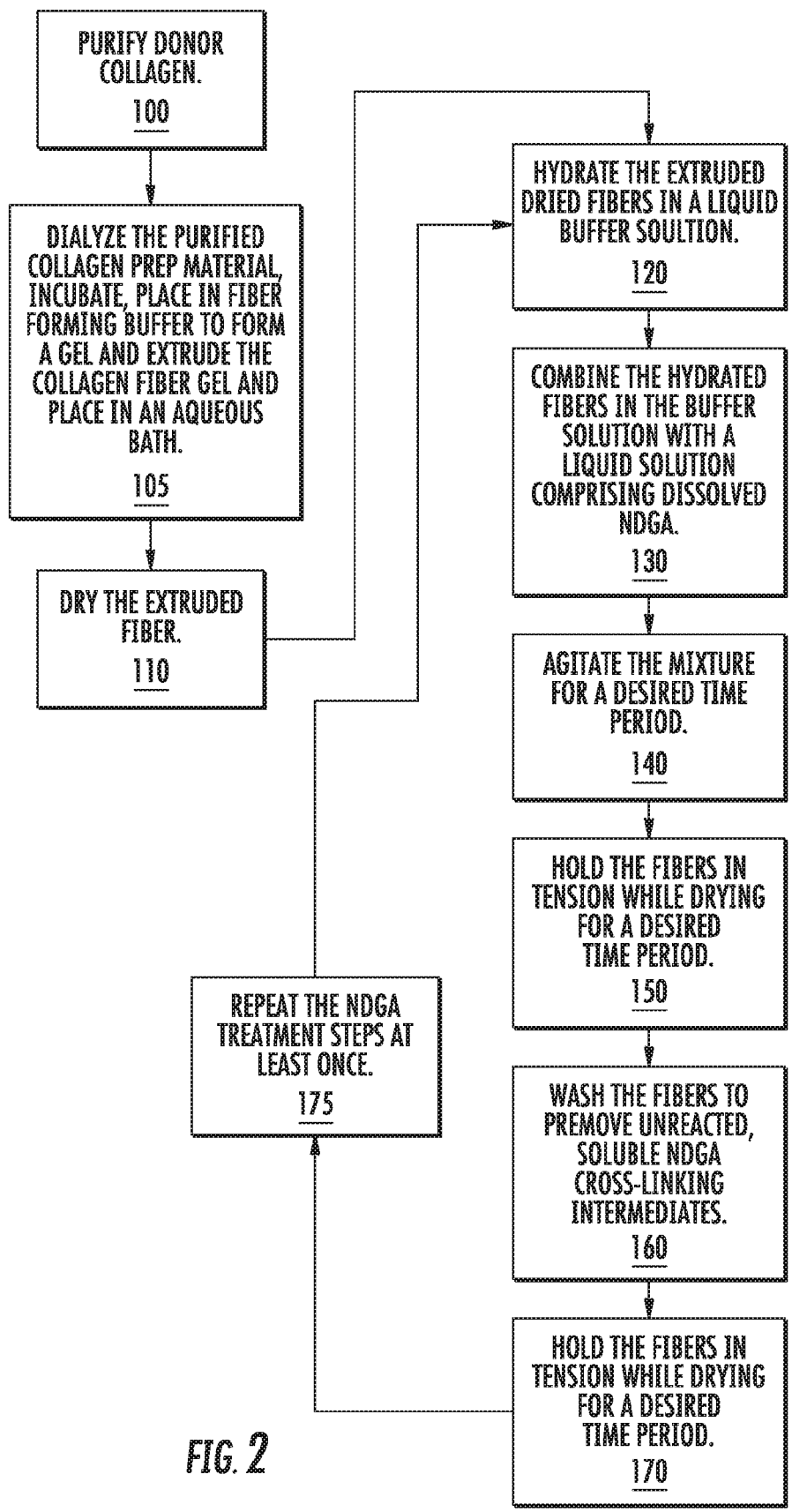
FIG. 2 is a flow chart of operations that can be used to carry out embodiments of the invention.
Figure 6:
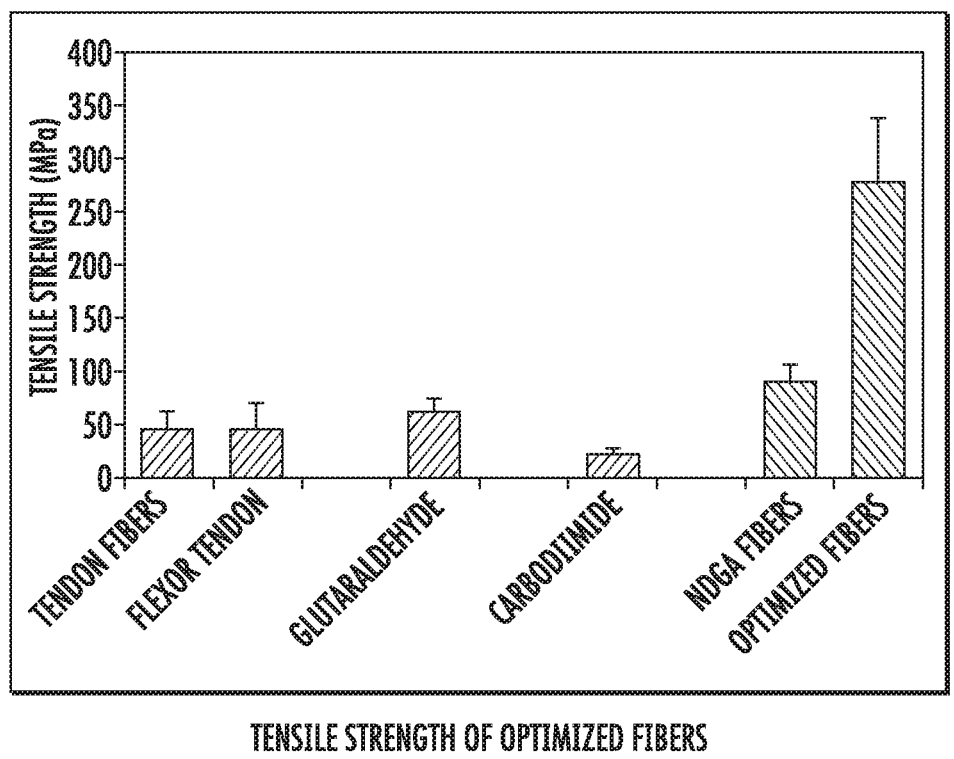
FIG. 6 is a graph of tensile strength (MPa) of high strength NDGA fibers relative to other fibers, including prior NDGA fibers, according to embodiments of the invention.

FIG. 2 illustrates operations that can be used to form NDGA-treated collagen fibers according to other embodiments of the invention. As shown, donor collagen material is obtained and purified as appropriate (block 100). The donor material can be from any suitable source. FIG. 6 illustrates different fiber tensile strengths (average) obtained using different donor collagen sources. The purified collagen preparatory material is dialyzed, incubated, then placed in a fiber-forming buffer that is then extruded (block 105).

Figure 3:
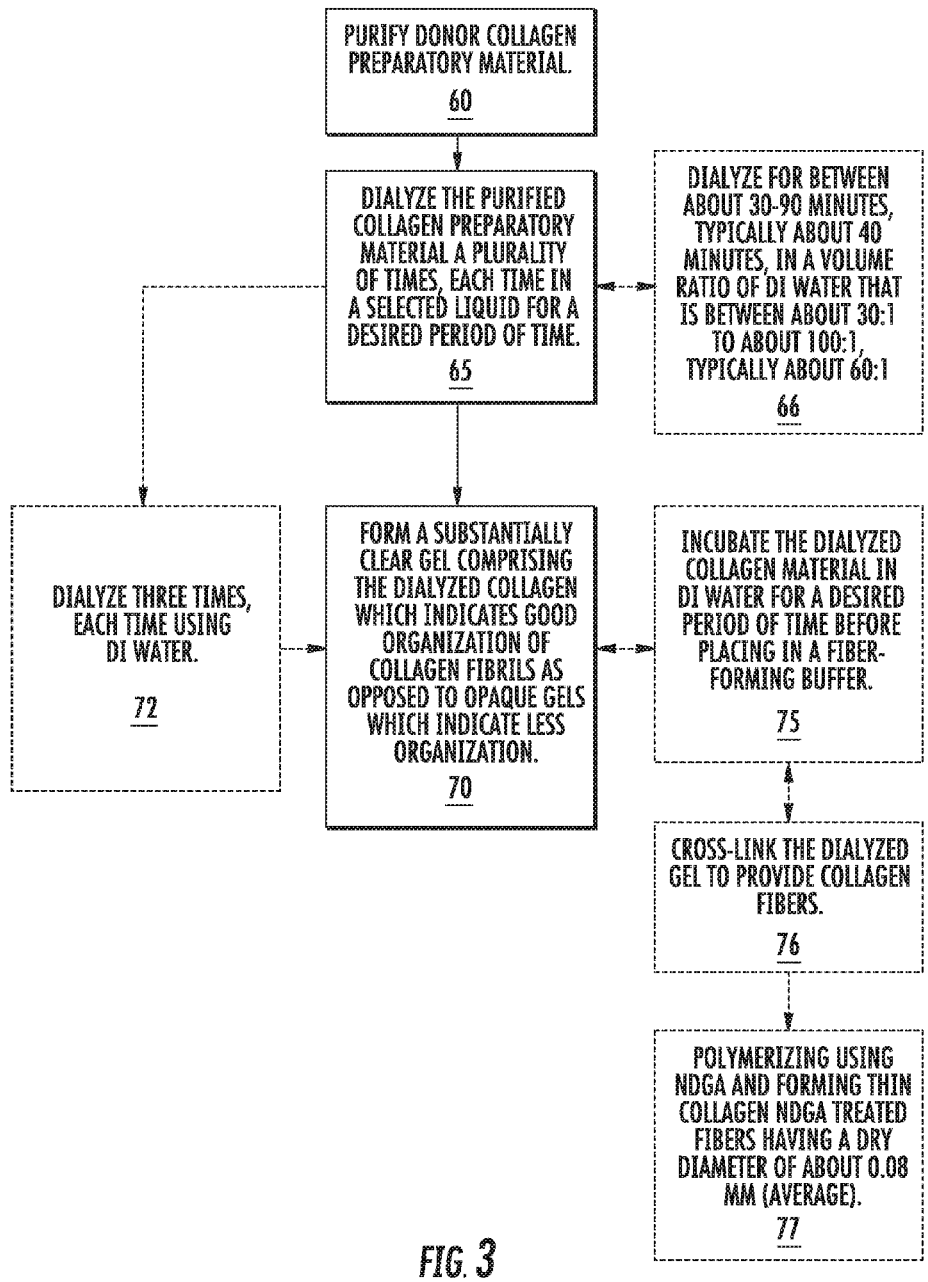
FIG. 3 is a flow chart of operations that can be carried out before cross-linking for improved organization of collagen fibrils in collagen preparatory material according to embodiments of the invention.

FIG. 3 illustrates operations that can be used to form improved organization of collagen fibrils using a dialyzing process. As noted above, preparatory donor collagen material can be purified (block 60). The purified collagen preparatory material is dialyzed a plurality of times in a selected liquid for a desired period of time (block 65). The dialyzing is typically repeated three times (block 72). The dialyzing can be carried out against dionized (DI) water in a volume ratio of between about 30:1 to about 100:1, typically about 60 to 1, for between about 30-90 minutes, typically about 40 minutes (block 66). The dialyzing can form a substantially clear gel of collagen fibrils indicating good organization (block 70), where opacity indicates less organization. The organization can help improve tensile strength of subsequently cross-linked fibers.

The dialyzed collagen material can be incubated for a desired time before placing in a fiber-forming buffer (block 75). The dialyzed gel can be cross-linked to provide collagen fibers for medical constructs (block 76). The polymerization (e.g., cross-linking) can be carried out using NDGA and the resultant NDGA treated collagen fibers can be relatively thin, such as, for example, about 0.08 mm dry diameter (on average) (block 77).

The incubation may be for at least about 24 hours, typically 24-48 hours, and may be at room temperature of between about 15-30° C., typically about 25° C. The dialysis process can be used before cross-linking for subsequent use with any suitable cross-linking materials, to promote collagen organization, such as, for example, and the process is not limited to NDGA, but may be useful with other materials, including, for example, glutaraldehyde. The dried collagen fiber can also be treated with other methods to improve the tensile properties of the fiber. The dried collagen fibers produced by the method(s) described herein can be cross-linked with agents such as glutaraldehyde, formaldehyde, epoxy resins, tannic acid, or any other chemical agent that produces covalent cross-links between collagen molecules within fibrils or between fibrils. Alternatively, the dried fiber can be treated to induce cross-linking between collagen molecules such as, but not limited to, one or more of a carbodiimide treatment, ultraviolet irradiation either with or without carbohydrates to initiate glycation adducts, and dehydrothermal treatment coupled with any of the aforementioned methods.

The fiber-forming buffer can include about 30 mM $NaH_2PO_4$, 140 mM NaCl, in a volume ratio of about 60 to 1, for between about 12-24 hours, typically about 16 hours at a slightly elevated temperature of about 37° C. The extrusion can be directed to enter directly or indirectly into an aqueous bath, such as a water or saline bath, and hung from one end portion. To remove from the bath, the extruded material can be lifted out of the bath at a slow rate of less than about 5 mm/min, typically about 1 mm/min. The extruded fibers can then be dried (block 110). To dry, the fibers may be hung or otherwise held for at least about 5 hours, typically for at least about 6 hours, such as between about 6-10 hours.

Referring again to FIG. 2, as shown, the extruded dried fibers can be hydrated in a liquid buffer solution (block 120). The hydration can be for between about 30 minutes to about 3 hours, typically about 1 hour, in a solution of at least 50 ml of buffer (such as 0.1 M $NaH_2PO_4$, pH 7.0) per gram of dry fiber. In some embodiments, the pH of the phosphate buffered solution can be increased to above pH 7 to a pH of about 11 or between 7-11, e.g., a pH of about 8.0, 9.0, 10.0 or 11.0.

The hydrated fibers in the buffer solution can then be combined with a liquid solution comprising (dissolved) NDGA (block 130). About 30 mg/ml of the NDGA can be dissolved in about 0.4 NaOH prior to combining with the buffer/fiber solution. The dissolved NDGA solution can be added in an amount of between about 3-4 mg NDGA per ml of buffer, such as about 0.1 M $NaH_2PO_4$. The NDGA and fiber solution can be agitated, shaken, centrifuged, rotated, oscillated or otherwise moved and/or mixed for a length of time (block 140), typically between about 12-48 hours, such as at least about or about 16 hours. As discussed above with respect to FIG. 1, the fibers can then be removed and held in tension (e.g., hung or stretched), during a drying operation (block 150), typically lasting at least about 2 hours. The (partially or wholly) dried fibers can then be washed to remove unwanted reaction products (block 160). Typically, the fibers are washed (agitated) in about 70% ethanol as also discussed above, then held in tension during a drying operation (block 170). The steps 120-170 can be repeated (block 175).

Figure 5:
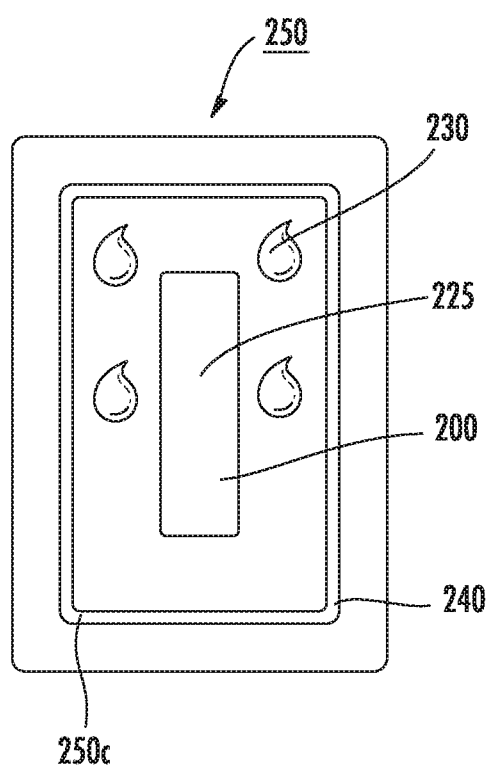
FIG. 5 is a schematic illustration of a medical kit comprising a high-strength NDGA-treated collagen construct according to embodiments of the invention.

FIG. 5 illustrates a medical kit 250 that includes a medical device or implant 225 with at least one NDGA-treated collagen fiber 200. The kit 250 may include other components, such as, for example, a container of surgical adhesive, sutures, suture anchors, and the like. The device or implant 225 may be held hydrated in a flexible sealed package of sterile liquid 230. The kit 250 may include a temperature warning so that the construct 225 is not exposed to unduly hot temperatures that may degrade the implant. A temperature sensor may optionally be included on the package of the kit (not shown) to alert the clinician as to any excessive or undue temperature exposure prior to implantation. For example, it may be desirable to hold or store the kit 250 (and implant or device 225) at a temperature that is less than about 37° C. and/or 100° F. prior to implantation. The kit 250 may be packaged in a housing with a temperature controlled or insulated chamber 250c to facilitate an appropriate temperature range.

Embodiments of the invention can form implants and/or medical devices using NDGA collagen fibers with different tensile strengths from a single source type, e.g., NDGA-treated bovine collagen, with both low strength, such as less than about 90 MPa tensile strength, typically between about 10 MPa and 90 MPa, and high strength fibers and/or using NDGA-treated collagen from more than one source type (e.g., bovine and echinoderm).

The present invention is explained in greater detail in the following non-limiting Examples.

EXAMPLES

FIG. 6 illustrates average tensile strength of NDGA-treated collagen fibers that can be produced according to embodiments of the invention. In some embodiments, the fibers can be produced by the below described 12 step process. The reference to the lower strength "NDGA fibers" in FIG. 6 refers to prior art fibers as described in U.S. Pat. No. 6,565,960 and/or Koob and Hernandez, *Material properties of polymerized NDGA-collagen composite fibers: development of biologically based tendon constructs*, Biomaterials, 2002 January; 23 (1): 203-12.

1. Purify Type I collagen from 8-9 month old fetal bovine tendons as previously described (Koob and Hernandez, Biomaterials 2002, supra).
2. Dilute the purified collagen prep with 3% acetic acid to a final concentration of 0.2% (weight/volume).
3. Place the purified collagen prep in 3.2 mm diameter dialysis tubes and dialyze 3 times against DI (di-ionized) water in a volume ration of 60 to 1 for 40 minutes each time.
4. Incubate in DI water for 36 hours at room temperature (25° C.)
5. Place in fiber-forming buffer of 30 mM $NaH_2PO_4$, 140 mM NaCl in a volume ratio of 60 to 1 for 16 hours at 37° C. This causes the collagen to form a gel within the dialysis tubes.
6. Extrude the collagen fiber gel into a water bath, hang from one end and lift out of the water bath at a rate of 1 mm/min and allow drying for at least 6 hours.
7. Hydrate the dried fibers for 1 hr in at least 50 ml of buffer (0.1 M $NaH_2PO_4$ pH 7.0) per gram of dry fiber.
8. Dissolve 30 mg/ml NDGA in 0.4 N NaOH
9. Add the dissolved NDGA solution to the buffer and fibers (use 3.33 mg NDGA per ml of 0.1 M $NaH_2PO_4$). Agitate for 16 hours
10. Hang for 2 hrs with a 6.7 gram weight clamped to the bottom to provide tension while drying.
11. Place in 50 ml of 70% ethanol per gram of dry fiber and agitate for 2 hrs of washing to remove any unreacted, soluble, NDGA cross-linking intermediates.
12. Dry again as per step 10 and repeat the NDGA treatment as per steps 7 through 9 above.

Figure 7:
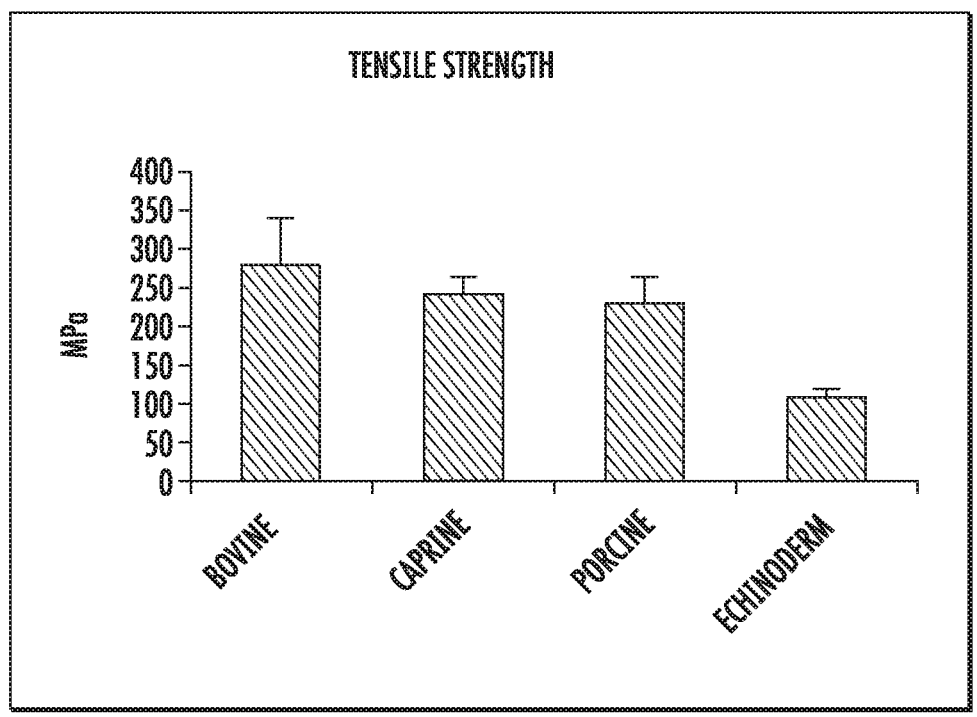
FIG. 7 is a graph of tensile strength (MPa) of fibers using collagen from different sources according to embodiments of the invention.

FIG. 7 illustrates different donor or starting collagen materials, including bovine, caprine, porcine and echinoderm produced according to the methods described herein and treated with NDGA having associated average tensile strength using manufacturing methods described herein. In the case of the echinoderm collagen fibers, the collagen fibrils were produced by water extraction of the sea cucumber dermis producing intact native fibrils according to published methods. See, Trotter, J. A., Thurmond, F. A. and Koob, T. J. (1994) *Molecular structure and functional morphology of echinoderm collagen fibrils*. Cell Tiss. Res. 275; 451-458.

NDGA treated collagen constructs have biocompatibility, suitable biomechanical properties and the potential for biologic in-growth of native tissue for long-term stability.

The foregoing is illustrative of the present invention and is not to be construed as limiting thereof. Although a few exemplary embodiments of this invention have been described, those skilled in the art will readily appreciate that many modifications are possible in the exemplary embodiments without materially departing from the novel teachings and advantages of this invention. Accordingly, all such modifications are intended to be included within the scope of this invention as defined in the claims. The invention is defined by the following claims, with equivalents of the claims to be included therein.

That which is claimed:

1. A method of manufacturing nordihydroguaiaretic acid (NDGA) polymerized collagen fibers, comprising:
    (a) treating collagen with a solution comprising NDGA to provide NDGA-treated collagen;
    (b) drying the NDGA-treated collagen while holding the NDGA-treated collagen in tension for a period of time;
    (c) washing the dried NDGA-treated collagen in a solution to remove unreacted soluble NDGA cross-linking intermediates;
    (d) drying the NDGA-treated collagen while holding the NDGA-treated collagen in tension for a period of time; and
    repeating steps (a)-(d) at least once to produce high-strength NDGA polymerized collagen fibers,
    wherein the high-strength NDGA polymerized collagen fibers have an average tensile strength of at least about 150 MPa.

2. A method according to claim 1, wherein the washing step is carried out using an ethanol solution.

3. A method according to claim 1, wherein the washing step comprises agitating the NDGA-treated collagen in an ethanol solution for between about 1-4 hours.

4. A method according to claim 1, wherein the drying steps are carried out while collagen fibers associated with the NDGA-treated collagen are held in tension for between about 1-5 hours.

5. A method according to claim 4, wherein the collagen fibers are held in tension for about 2 hours during the drying steps.

6. A method according to claim 1, wherein the drying steps include holding the NDGA-treated collagen fibers in tension with a tensile force of between about 2 grams to about 10 grams.

7. A method according to claim 1, wherein the drying steps include clamping bottom portions of collagen fibers associated with the NDGA-treated collagen to a weight of between about 5-10 grams to apply a tensile force.

8. A method according to claim 1, further comprising, after the steps are repeated at least once, forming a bioprosthesis using the high-strength NDGA polymerized fibers.

9. A method according to claim 8, wherein the bioprosthesis is a ligament bioprosthesis that has a tensile strength of between about 180-280 MPa, and a stiffness and dynamic flexibility that meets or exceeds that of a natural ligament.

10. A method according to claim 8, wherein the bioprosthesis has a tensile strength between about 180-280 MPa, and a stiffness and dynamic flexibility that meets or exceeds that of a natural tendon.

11. A method according to claim 10, wherein the NDGA polymerized collagen fibers have a dry diameter on average of about 0.08 mm and a wet diameter on average of about 0.13 mm.

12. A method of organizing collagen before cross-linking, comprising:
   purifying donor collagen preparatory material;
   dialyzing the purified collagen preparatory material at least three times against deionized water in a volume ratio of between about 30:1 to about 100:1, for between about 30-90 minutes to form a dialyzed collagen material; and
   forming a substantially clear gel using the dialyzed collagen material thereby indicating improved organization of collagen fibrils.

13. A method according to claim 12, wherein the dialyzing is carried out three times against deionized water in a volume ration of about 60 to 1 for about 40 minutes.

14. A method according to claim 12, further comprising incubating the dialysized collagen material for at least about 24 hours at a temperature of between about 15-30° C. to form incubated collagen material; then
   placing the incubated collagen material in a fiber forming buffer to form a buffered collagen material;
   extruding the buffered collagen material;
   cross-linking the buffered collagen material; then
   forming polymerized collagen fibers.

15. A method according to claim 14, wherein the cross-linking is carried out using NDGA, and wherein the forming step forms NDGA treated collagen fibers having a dry diameter of about 0.08 mm, on average.

* * * * *

UNITED STATES PATENT AND TRADEMARK OFFICE
CERTIFICATE OF CORRECTION

PATENT NO. : 10,472,409 B2
APPLICATION NO. : 15/431516
DATED : November 19, 2019
INVENTOR(S) : Koob et al.

It is certified that error appears in the above-identified patent and that said Letters Patent is hereby corrected as shown below:

In the Specification

Column 1, Line 10: delete "14/964,756" and insert -- 11/964,756 --

In the Claims

Column 11, Line 14, Claim 13: delete "ration" and insert -- ratio --

Signed and Sealed this
Fifth Day of May, 2020

Andrei Iancu
*Director of the United States Patent and Trademark Office*